(12) United States Patent
Dorairaj et al.

(10) Patent No.: US 7,988,839 B2
(45) Date of Patent: Aug. 2, 2011

(54) CAPILLARY ELECTROPHORESIS SYSTEMS AND METHODS

(75) Inventors: Rathissh Dorairaj, Hillsboro, OR (US); Robert S. Keynton, Louisville, KY (US); Thomas J. Roussel, Louisville, KY (US); Mark M. Crain, Georgetown, IN (US); Douglas J. Jackson, New Albany, IN (US); Kevin M. Walsh, Louisville, KY (US); John F. Naber, Goshen, KY (US); Richard P. Baldwin, Louisville, KY (US); Danielle B. Franco, Mount Washington, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 1262 days.

(21) Appl. No.: 11/524,357

(22) Filed: Sep. 20, 2006

(65) Prior Publication Data

US 2011/0155575 A1 Jun. 30, 2011

Related U.S. Application Data

(60) Provisional application No. 60/718,863, filed on Sep. 20, 2005.

(51) Int. Cl.
 *G01N 27/26* (2006.01)
(52) U.S. Cl. ........................................ 204/451; 204/601
(58) Field of Classification Search .................. 204/451, 204/601
See application file for complete search history.

(56) References Cited

U.S. PATENT DOCUMENTS

| | | | |
|---|---|---|---|
| 5,858,187 A | 1/1999 | Ramsey et al. | |
| 5,932,315 A | 8/1999 | Lum et al. | |
| 5,942,093 A | 8/1999 | Rakestraw et al. | |
| 6,361,671 B1 | 3/2002 | Matthies et al. | |
| 6,685,809 B1 | 2/2004 | Jacobson et al. | |
| 6,939,451 B2 | 9/2005 | Zhao et al. | |
| 7,344,628 B2 | 3/2008 | Jackson et al. | |
| 2004/0134845 A1* | 7/2004 | Paul et al. ................... | 210/198.2 |

FOREIGN PATENT DOCUMENTS

| | | |
|---|---|---|
| DE | 19949538 | 5/2001 |
| GB | 2 302 590 | 1/1997 |
| WO | WO 96/04547 | 2/1996 |

(Continued)

OTHER PUBLICATIONS

Dorairaj, R., et al., "Dual Capillary Electrophoresis Devices with Electrochemical Detection on a Single Platform", Proceedings of the 3rd Annual International IEEE EMBS Special Topic Conference on Microtechnologies in Medicine and Biology, May 12-15, 2005, p. 15-17.*

(Continued)

*Primary Examiner* — Alexa D Neckel
*Assistant Examiner* — J. Christopher Ball
(74) *Attorney, Agent, or Firm* — Greer, Burns & Crain Ltd.

(57) ABSTRACT

An embodiment of the invention is directed to a capillary electrophoresis apparatus comprising a plurality of separation micro-channels. A sample loading channel communicates with each of the plurality of separation channels. A driver circuit comprising a plurality of electrodes is configured to induce an electric field across each of the plurality of separation channels sufficient to cause analytes in the samples to migrate along each of the channels. The system further comprises a plurality of detectors configured to detect the analytes.

22 Claims, 7 Drawing Sheets

FOREIGN PATENT DOCUMENTS

| WO | WO 97/36170 | 10/1997 |
|----|-------------|---------|
| WO | WO 98/09161 | 3/1998 |
| WO | WO 00/77509 | 12/2000 |
| WO | WO 01/51918 | 7/2001 |

OTHER PUBLICATIONS

Keynton, R. S., et al., "Design and Development of Microfabricated Capillary Electrophoresis Devices with Electrochemical Detection", Analytica Chimica Acta, vol. 507, No. 1, Apr. 1, 2004, p. 95-105.*

Voegel, P.D., and R.P. Baldwin, "Electrochemical detection in capillary electrophoresis with dual-parallel on-capillary electrodes", Electrophoresis, vol. 19, 1998, p. 2226-2232.*

Gyros AB, "Microfluidics in a Rotating Disc," Presented at "Microfluidics for Lab-on-a-Chip (LOC) Technology" Washington DC Sep. 9-11, 2001, www.gyrosmicro.com.

T. Roussel, et al. "A Capillary electrophoresis platform with "on-chip" electrochemical detection: experimental and computational flow studies," Nov. 2001, Micro-Electromechanical Systems, vol. 3, pp. 781-785.

K. Seiler, et al., "Planar glass chips for capillary electrophoresis: repetitive sample injection, quantification, and separation efficiency," May 15, 1993, Analytical Chemistry, American Chemical Society, Columbus, US, vol. 65 No. 10, pp. 1481-1488.

Conklin, J., M. Crain, R. Pai, M. Martin, et al. "Alternative Fabrication Methods for Capillary Electrophoretic Device Manufacturing," printed from www.mecca.spd.louisville.edu/~lad-on-a-chip/xvz__pubs.html, Louisville, KY: University of Louisville (2001) The month of publication is not presently available, but the year of publication is sufficiently earlier than the effective U.S. filed and any foreign priority date so that the particular month of publication is not in issue.

Pai, R., T. Roussel, Jr., M. Crain, D. Jackson, et al. "Integrated Electrochemical Detection for Lab on a Chip Analytical Microsystems," printed from www.mecca.spd.louisville.edu/~lad-on-a-chip/xyz__pubs.html Louisville, KY: University of Louisville (2001) The month of publication is not presently available, but the year of publication is sufficiently earlier than the effective U.S. filing date and any foreign priority date so that the particular month of publication is not in issue.

Seiler, et al. Electroosmotic Pumping and Valveless Control of Fluid Flow Within a Manifold of Capillaries on a Glass Chip, Anal. Chem, 1994, 66, 3485-3491. The month of publication is not presently available, but the year of publication is sufficiently earlier than the effective U.S. filing date and any foreign priority date so that the particular month of publication is not in issue.

* cited by examiner

CAPILLARY ELECTROPHORESIS SYSTEMS AND METHODS

RELATED APPLICATIONS

The present application claims priority on U.S. Provisional Application Ser. No. 60/718,863 filed Sep. 20, 2005.

STATEMENT OF GOVERNMENT INTEREST

This invention was made with government assistance provided by the National Science Foundation EPSCOR under Contract No. 6016955, and provided by the Department of Energy EPSCOR under Contract No. 46411101095. The government has certain rights in this invention.

BACKGROUND

Advancements in the fields of analytical chemistry and biomedical technology have stressed the need for more efficient means of analyses with faster analysis times, smaller sample and reagent consumption, higher efficiency, greater apparatus portability and easier use. Capillary Electrophoresis (CE) is a commonly used separation technique, which makes use of differences in the charge ratio of components in a mixture. CE generally includes a capillary placed between two electrodes linked by a voltage source. The capillary is filled with an electrolyte such as an aqueous buffer solution. A sample of a material to be tested is also introduced into the capillary.

Testing is initiated by applying an electric field between the electrodes. All ions, positive or negative, are pulled through the capillary in the same direction by electroosmotic flow. The field also causes the components of the material being tested, referred to as analytes, to separate as they migrate toward the cathode due to their electrophoretic mobility. The rate of migration differs depending on the analytes particular electrokinetic mobility. These analytes are detected near the outlet end of the capillary. Analytes can generally be identified through knowledge of the electric field applied, the geometry of the capillary, the distance of migration, and the time required to migrate that distance. For example, in a mixture of dopamine and catechol, dopamine having the higher electrokinetic mobility would reach the cathode faster than catechol, which has a lower electrokinetic mobility. Separation by capillary electrophoresis can be detected by several detection methodologies, including by way of example but not limited to, ultraviolet (UV) or UV-Vis absorbance, fluorescence detection, electrochemical detection or mass spectrometery.

One limitation of some capillary electrophoresis systems and methods is that samples which contain analytes with equal or near-equal mobilities cannot be readily separated. For two analytes having substantially equal mobilities, for example, migration in a CE capillary or microchannel will be at essentially the same velocity and therefore may be difficult to conclusively detect. Detection errors may result, such as inaccurately detecting the concentration of analytes, or analyte misidentification.

In addition, like many analysis techniques, CE procedures often call for highly reliable test results. Such reliability may require redundant testing of samples. Many current systems and techniques require multiple test runs or multiple samples to accomplish redundant results. Multiple test runs or samples increase total testing time and introduce a risk that the sample may be contaminated or otherwise be inconsistent between test runs. In addition, larger volumes of sample are required, which may or may not always be available and will increase the cost of the process.

Still an additional problem with some CE systems and methods of the prior art related to achieving test analyte samples (or "plugs") in a detection channel having a good geometry. Some systems of the prior art use a configuration that provides poorly defined sample plugs. Other systems require multiple power supplies to generate multiple electric fields to produce sample plugs, which results in complex and extensive circuitry and system size as well as other disadvantages. These and other problems make some CE systems of the prior art ill-suited for field and related applications where portability is desired.

These and other problems remain unresolved in the art.

SUMMARY

One example embodiment of the invention provides a device for performing dual capillary electrophoresis with electrochemical detection (ECD) on a single platform.

One example embodiment of the invention is directed to a capillary electrophoresis apparatus comprising a plurality of separation channels configured to carry a buffer solution and a sample loading channel communicating with each of the plurality of separation channels. A loading circuit comprising a plurality of electrodes is configured to induce an electric field across the sample loading channel sufficient to deliver a sample to the plurality of separation channels. The system further comprises a plurality of detectors, one each of the plurality of detectors proximate to each of the separation channels and configured to detect the analytes. A driver circuit comprising a plurality of electrodes is configured to induce an electric field across each of the plurality of separation channels, the electric field useful to cause analytes from the samples to migrate in each of the plurality of separation channels towards one of the detectors. The system further comprises at least a controller configured to record data from each of the plurality of detectors, to control the plurality of detectors, and to control the driver circuit.

An additional example embodiment of the invention is directed to a method for performing capillary electrophoresis, and comprises the steps of introducing one sample into a sample loading micro-channel and applying a first electric field across the sample loading micro-channel to cause the sample to migrate through the micro-channel and into a plurality of separation micro-channels. A step is performed of applying a second electric field across the plurality of separation micro-channels to cause analytes from the one sample to migrate through the plurality of separation micro-channels. The analytes are identified proximate to the end of each of the separation micro-channels using a detector positioned proximate to each of the ends.

Another example embodiment of the invention provides a lab-on-a-chip (LOC) micro analytical device, such as a soda-lime glass-based or polymer-based LOC, which includes the capability to simultaneously separate and detect multiple chemical/biochemical analytes in a dual capillary electrophoresis system. The LOC preferably includes at least two separation channels and therefore will enable the separation and detection of multiple analytes where the analytes require different electrode materials, such as, for example, analytes that have equal mobilities; and for a redundancy in instrumentation for analyte detection verification. Another potential advantage of this approach is the possibility for reducing analysis times. One electrochemical detector may be suitably modified for detection of a particular analyte, while the other for another analyte, thus reducing the dependence on separation for multiple analyte detection.

In this example invention embodiment, end-channel detection of each of the analytes is accomplished by electrochemical detection, which may include three electrodes referred to for convenience as work, reference and auxiliary. A constant voltage is applied between the work and reference electrodes, which causes a constant base current flow through the two electrodes. When an analyte travels over the work electrode, the charge of the analyte causes it to participate in an oxidation/reduction reaction with the work electrode. The electrons gained or lost by the work electrode cause an increase or decrease in current, which indicates the presence of an analyte flowing through the micro-channel and quantifies the same.

An example capillary electrophoresis system of the invention, including an electrochemical detector, when combined with microfabrication, can offer some advantages over absorbance or fluorescence detection methodologies and other separation techniques. These can include simpler electronics, portability, smaller size (microchannels having a width of approximately 50 micrometers), minimal reagent and sample consumption on the order of nanoliters, as well as ease of use.

Embodiments of the invention contemplate use as a diagnostic tool, whereby the device could be used to analyze blood or other body fluids to determine composition, and thereby detect cause of illness in a patient or for astronauts in space due to the small size and relative ease of use. Other embodiments contemplate the possibility for bed-side analysis for critically ill patients or on-site field testing in the case of environmental or chemical and/or bio-warfare testing, since the device and the associated electronics are compact, portable and the results are immediate. Still other embodiments contemplate chemical analysis to determine composition of a solution under analysis. This application could be used by chemical industries, environmental agencies, Departments of Homeland Security and Defense, research laboratories and hospitals. Yet other embodiments include DNA analyses and protein and cell lysing.

DETAILED DESCRIPTION

Figure 1:
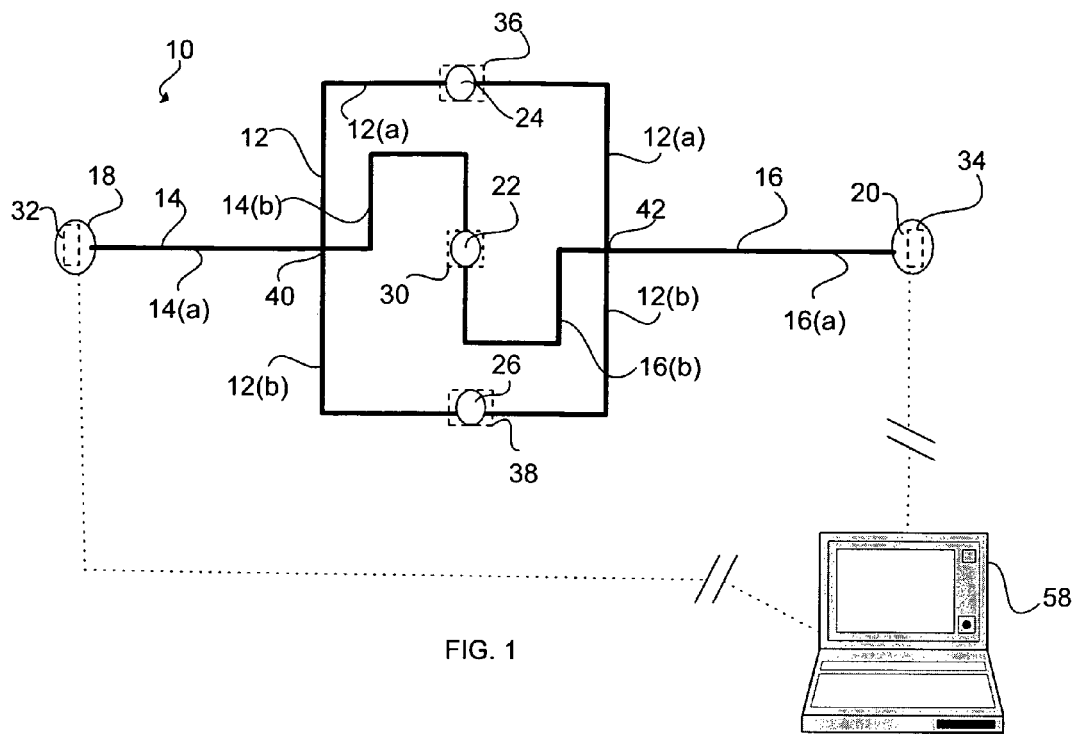
FIG. 1 is a schematic of an example capillary electrophoresis system.

FIG. 1 is a schematic of one example capillary electrophoresis system 10 of the invention. It includes a sample loading micro-channel 12 and a pair of separation micro-channels 14 and 16. Detector systems 18 and 20 are proximate to the end of the separation micro-channels 14 and 16, respectively. The detector systems 18 and 20 may be any of a number of suitable systems and include various components as will be described in detail below.

The separation micro-channels 14 and 16 contain a buffer solution, which is supplied from a buffer reservoir 22 communicating with the separation micro-channels 14 and 16. Any of several buffer solutions as known in the art are suitable for use with the system 10. Examples include electrolytes with a pH >2, with particular examples including mixtures of sodium borate and dodecyl sulphate, phosphate buffer (potassium phosphate+sodium phosphate), Tris(hydroxymethyl aminomethane), boric acid/EDTA buffer and MES (morpholinoethanesulphonic acid)+$LiOH.H_2O$.

The separation micro-channels 14 and 16 can be considered to be continuous with one another, connecting through the buffer reservoir 22. Sample is provided to the sample loading micro-channel 12 from a sample reservoir 24 communicating therewith. The sample loading micro-channel 12 also communicates with a waste reservoir 26.

Driver circuit electrodes are arranged about the separation micro channels 14 and 16, including a centrally located anode 30 and two cathodes 32 and 34. The driver circuit electrodes are in wetted contact with the buffer solution. The electrodes 32 and 34 have been illustrated in dashed to indicate that they may be arranged with the detector systems 18 and 20. As will be discussed below in detail when illustrating example detector systems 18 and 20, the electrodes 32 and 34 may be contained in detector reservoirs provided with each of the systems 18 and 20.

The anode 30 is located centrally between the separation micro-channels 14 and 16. It has been represented in dashed lines in FIG. 1 to indicate that it may be vertically stacked with the buffer reservoir 22, and/or a portion of the micro-channels 14 and 16 when the capillary electrophoresis system 10 is configured on a micro-chip. For example, in some micro-chip and fabricated board applications, the anode 30 might be a thin conductor layer, with an example being about 300 nm thick, below a substrate or patterned onto the substrate. The reservoir 20 might be arranged directly above the conductor.

In some embodiments, the anode 30 may be a thin metal layer that is deposited within and at the base of the reservoir 22 to form at least a portion of a reservoir "floor." It has been illustrated as a rectangle in dashed underlying the reservoir 22 in FIG. 1 for clarity. The cathodes 32 and 34 may also be configured in this vertically stacked manner underlying or on a substrate in which the micro-channels 14 and 16 are etched.

Loading circuit electrodes are arranged about the sample loading micro-channel 12, including an anode 36 and a cathode 38. The anode 36 and cathode 38 have been shown in dashed line similar to the driver anode 30 to indicate that they are within (or underlying) the reservoirs 24 and 26, respectively. The anode 36 and cathode 38 can be thin conductor layers. Examples include metal layers of about 300 nm thickness on all or a portion of the floor of the reservoirs 24 and 26, respectively, and are thereby in contact with the sample solution. These reservoirs can be drilled, etched or otherwise formed in a substrate overlaying the anode 36 and cathode 38 conductors, or the anode and cathode may form thin metal layers deposited at the base of the reservoirs 24 and 26. Other configurations are possible, with an example being locating the electrodes 36 and 38 in a location removed from the reservoirs 24 and 26.

It will be appreciated that all of the electrodes 30-38 of the example system 10 are in contact with fluid (sample and/or buffer) in order to provide good electrical contact. The various electrodes may be sized as desired and according to design parameters of the application. If the voltages to be applied are substantial, a suitable size is recommended to avoid the risk of bubble generation from electrolysis.

As will be described in greater detail below, during operation the electrodes of the example system 10 are useful to establish an electrical field in either a sample loading mode or driving (i.e., detection) mode. This is accomplished by applying a negative voltage to the waste reservoir 26 in the sample loading mode (to effectively "pull" fluid from the detectors 18/20, sample reservoir 24, and buffer reservoir 22), or a positive voltage to the buffer reservoir 22 in the driving (i.e., detection) mode (to effectively "push" fluid from the buffer reservoir 22 to the detectors 18/20, sample reservoir 24, and waste reservoir 38.

The loading circuit is configured to cause analytes from the sample reservoir 24 to migrate into the sample loading micro-channel 12, through intersections 40 and 42 where the loading micro-channel 12 communicates with the separation micro-channels 14 and 16 and finally into the waste reservoir 26. This migration can be caused through the application of an electric field between the anode 36 and cathode 38 which can cause sample analytes to migrate towards the cathode 38.

The structure of the sample system 10, including channels 12, 14 and 16 as well as its loading and driver circuits, is advantageously configured to provide highly balanced flow as well as discrete, symmetric sample plugs. This is achieved, at least in part, through the configuration of the channels 12-16 and individual legs that define them.

The sample injection micro-channel 12 can be described as being defined by a plurality of legs 12(*a*) and 12(*b*). First legs 12(*a*) extend between the sample reservoir 24 and the intersections 40 and 42. Second legs 12(*b*) extend between the waste reservoir 26 and the intersections 40 and 42. Likewise, the separation micro-channels 14 and 16 may be considered to be defined by portions 14(*a*) and 14(*b*), and 16(*a*) and 16(*b*), respectively. Legs 14(*a*) and 16(*a*) extend between the separation micro-channel ends 44 and 46 and the intersections 40 and 42, respectively; while legs 14(*b*) and 16(*b*) extend between the intersections 40 and 42 and the buffer reservoir 22. Legs 14(*b*) and 16(*b*) communicate with one another through the buffer reservoir 22.

In the example system 10 of FIG. 1, the electrical resistance of each of the legs 12(*a*), 12(*b*), 14(*b*), and 16(*b*) when measured end-to-end are substantially equal when they contain the same fluid or different fluids having similar electrical resistance properties (with an example being when the legs contain one of either the sample or the buffer solutions). Further, the resistance of each of these legs 12(*a*), 12(*b*), 14(*b*), 16(*b*) may also be substantially equal to the resistance of each of the legs 14(*a*) and 16(*a*). Configuring these channels to have equal resistance is useful to achieve well balanced current flows in all micro-channels, including their individual legs, as well as for other purposes.

For example, this is useful to produce a substantially symmetrical and concentrated sample "plug" (or "good plug") originating from intersection 40 and 42. This results when equal voltage potentials are applied using the driver circuit electrodes 30, 32 and 34 across combinations of legs [(14(*a*) or 16(*a*)) and 12(*b*)], legs [(14(*a*) or 16(*a*)) and 12(*a*)], legs [14(*a*) and 14(*b*)], and of legs [16(*a*) and 16(*b*)]. Therefore, substantially equal currents (which are analogous to analytes/buffer flow) flow through the intersections 40 and 42 into legs connected thereto. This results in a highly symmetric sample plug. Since it is the sample plug that migrates towards and is detected by the detector systems 18 and 20, it is desirable to spatially constrain the sample plug as much as possible.

As used herein, the term "symmetrical plug" is intended to be broadly interpreted as referring to a well defined geometric (and hence volumetric) shape. One example is a generally triangular plug resulting in the vertex (on the 12(*b*) side) being in the middle of the microchannel along its width. If the flow from the sides are minimized while still "containing" the sample stream, the plug would approach a square. This is desirable, since if the sample stream freely diffused from the intersections 40 and 42 into the channels 14(*a*)-(*b*) and 16(*a*)-(*b*), the volume of sample would be difficult to determine. By substantially containing the sample stream in the intersections 40 and 42 and measuring the channel currents (which are proportional to flow), the volume of a sample plug can be approximated.

If on the other hand, no field is applied across combinations of legs [(14(*a*) or 16(*a*)) and 12(*b*)], and [(14(*a*) or 16(*a*)) and 12(*a*)], the sample plug might enter 14(*a*) and 16(*a*) from intersection 40 and 42 under effects of lateral diffusion and therefore form a less symmetric plug (or "bad plug") having a diminished sample concentration. This can complicate detection and lead to unknown quantities of sample in the plug. Also, these effects and can lead to loss of sample to 14(*b*) or 16(*b*) during the driving mode.

Setting the electrical resistance of the legs 12(*a*), 12(*b*), 14(*a*), 14(*b*), 16(*a*) and 16(*b*) substantially constant in some example systems of the invention provides other benefits as well. As an example, this configuration eliminates the need for individual power supplies at each reservoir to achieve a focused injection. The equal channel resistance configuration of some example invention embodiments is able to operate using only a single power supply and still achieve a substantially balanced flow and resultant good plug. A single power supply may be advantageous to simplify the complexity of the circuitry, reduce the cost of the system, and enhance portability of the device.

It will be appreciated that given a particular contained fluid, the electrical resistance of the respective leg generally depends on the geometry of the particular leg 12(*a*)-(*b*), 14(*a*)-(*b*) and 16(*a*)-(*b*). Although the path of the leg (including bends and the like) can also be a factor, for practical purposes the determining factors can be defined as the length of the leg and the cross sectional area.

Setting the length and cross sectional area of each of the individual legs 12(*a*)-(*b*), 14(*a*)-(*b*) and 16(*a*)-(*b*) substantially equal will be useful to achieve substantially equal electrical resistances over the length of the individual legs. This condition is satisfied by the system illustrated in FIG. 1 (note that this and other FIGS. may not be drawn precisely to scale; each of legs 12(*a*)-(*b*), 14(*a*)-(*b*) and 16(*a*)-(*b*) are intended to be substantially equal in end-to-end length). This explains the right angled turns that the third legs 14(*b*) and 16(*b*) follow between the intersections 40 and 42 and the buffer reservoir 22.

Figure 2:
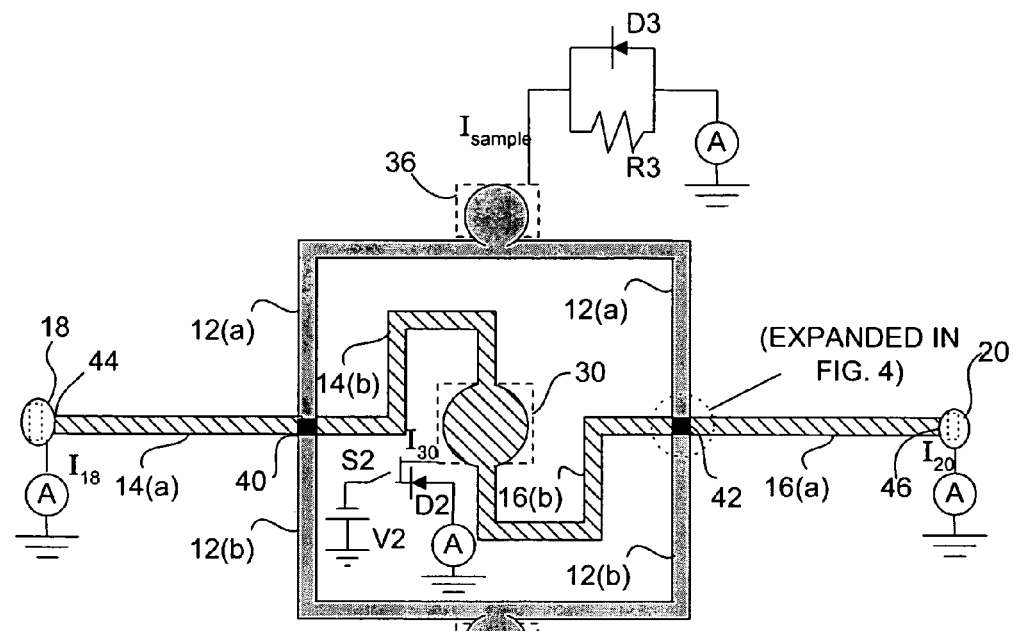
FIG. 2 is a schematic of the example capillary electrophoresis system of FIG. 1 illustrating sample and buffer solution at the end of a sample loading mode.
Figure 3:
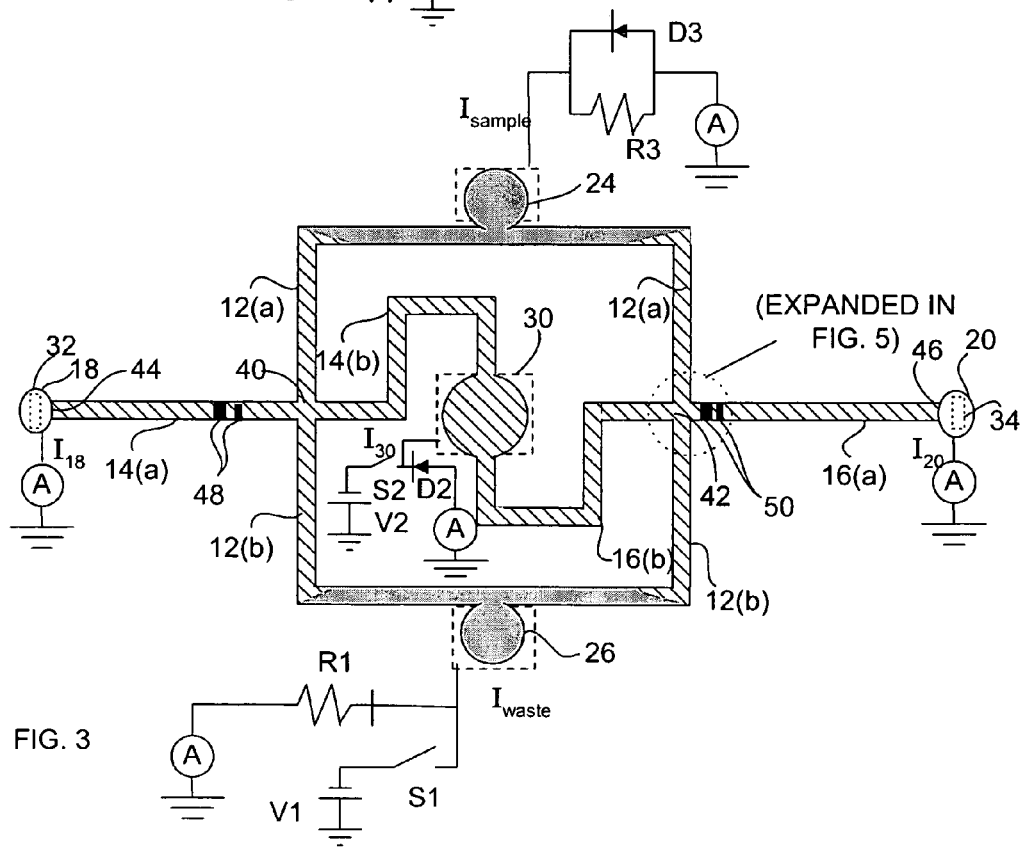
FIG. 3 is a schematic of the example capillary electrophoresis system of FIG. 1 illustrating sample and buffer solution during operation of a driver circuit.

Achieving a balanced flow as well as a symmetric and discrete plug using the example system 10 can be further illustrated through consideration of FIGS. 2-3. FIG. 2 illustrates the system 10 in loading mode. Presence of sample in the sample loading micro-channel 12 has been indicated with gray shading and presence of the buffer solution in the separation micro-channels 14 and 16 with a cross hatch pattern. As shown in FIG. 2, operation of the loading circuit anode 36 and cathode 38 generates an electric field which has caused sample to migrate from the sample reservoir 24 towards the waste reservoir 26 and thereby caused the loading micro channel 12, including intersections 40 and 42, to be substantially filled with sample.

Prior to operation of the loading circuit electrodes 36 and 38, micro channel 12 was filled with buffer solution. The concentration of the sample is typically much less than the concentration of the buffer solution, with the result that the electrical resistance of the solution does not change significantly with or without the sample (since sample concentration is very low in the buffer).

In the intersections 40 and 42 where the sample loading micro-channel 12 intersects with and communicates with the separation micro-channels 14 and 16, sample is present as has been indicated with black shading. The composition within the intersections 40 and 42 may be a mixture between sample and buffer. The portion of sample that exists in these intersection regions 40 and 42 may be referred to as a "plug."

Note that during operation of the loading circuit electrodes 36 and 38, some migration of analytes within the sample may occur. Accordingly, there is a risk that the composition of the sample across the loading micro-channel 12 may vary somewhat from sample reservoir 24 to waste reservoir 26. It has been discovered that operating this circuit for a sufficient time reduces this risk and causes the composition of the sample stream to be substantially uniform. Sufficient times will vary with various design parameters, but in some embodiments of the invention time periods of about 90-120 seconds is adequate, while in other example systems 4 minutes or more, and about 5 minutes or more, have been found to be sufficient to provide a substantially uniform composition. Particular time required can be empirically determined, and will vary according to sample composition, loading voltage used, buffer concentration, chip geometry, and like parameters.

FIG. 2 also provides detail of example electrical operation and circuitry of the loading electrodes 36 and 38. As will be described in detail herein below, both the driver circuit electrodes and loading circuit electrodes may utilize a single power supply. In the sample loading mode, a negative voltage from a source V1 is applied to the waste reservoir electrode 38 by closing relay S1 (effectively switching back from the "other" mode in a single power supply configuration—i.e. when the single power supply is on, it is either powering the loading circuit electrodes or the driver circuit electrodes—there is no standby mode). Diode D1 is reverse biased to block any current from flowing to an ammeter circuit in this mode. The sample reservoir 24, a reservoir at detector 18, and a reservoir at detector 20 are held at circuit ground potential using electrodes connected to ammeter circuits. The diodes D3 and D2 are forward biased and provide a low resistance path to the series connected ammeter circuits (transimpedance amplifier that converts current to voltage).

In the example loading operation illustrated by FIG. 2, the electric field across channel 14(a) equals the field across 14(b) due to the equal channel length and their effective parallel connection between intersection 40 and ground. Likewise, the fields established across 16(a) and 16(b) are equal. If channels 14(a) and (b) have equal cross sectional geometry they will produce the same electroosmotic flow. The equal flow from these legs defines and contains the analyte sample flowing from leg 12(a) at the channel intersection 40. An identical result occurs at intersection 42.

Current $I_{waste}$ is about Y2 the magnitude of current $I_{sample}$ and $I_{30}$. The current flowing in channel legs 12(a) and 14(b) is substantially equal to that flowing in 14(a). The magnitude of the current flowing in 12(b) is the sum of the currents flowing in 12(a), 14(a), and 14(b). The right hand side of the system 10 (channels 16(a)-(b) and 12(a)-(b) right side) shares the same relationship. The currents in each channel may be measured as a method to monitor the flows in all channels to ensure balanced flow.

FIG. 3 illustrates operation of the driver circuit, including the anode 30 and cathodes 32 and 34. This may be considered to occur sequentially after the operation of the loading circuit described above with reference to FIG. 2. The driver circuit electrodes are configured to apply electric fields across each of the separation channels 14 and 16. As a potential is applied between the anode 30 and each of the cathodes 32 and 34, an electric field spans each of the separation micro-channels 14 and 16. The electric field causes different analyte components of the sample plug to separate from one another as they migrate toward the cathodes 32 and 34 due to their different electrophoretic mobilities. The degree of separation between analytes varies with their differing rate of migration; analytes with higher mobilities will arrive at the detector systems 18 and 20 sooner than analytes with lower mobilities.

The illustrative schematic of FIG. 3 shows the state of the system 10 after the loading circuit has been switched to separation mode where a potential has been applied between the centrally located anode 30 and each of the cathodes 32 and 34. The same power supply may be used to power this circuit as was used to power the loading circuit. Under influence of these electric fields, two sets of analytes 48 and 50 migrate along each of the separation channels 14 and 16 towards the channel ends 44 and 46 and detector systems 18 and 20.

FIG. 3 illustrates the state of the sample loading micro-channel 12 following activation of the driver circuit. In particular, buffer solution supplied from the buffer reservoir 22 and migrating outward from the intersections 40 and 42 has partially filled the sample loading micro-channel 12. Because the reservoirs 24 and 26 are grounded, the buffer solution migrates from the separation micro-channels 14 and 16 towards these reservoirs 24 and 26 as the electric field is applied across the separation micro-channels 14 and 16.

With regard to the configuration of the electrical circuitry of the example system 10 in the detection mode, a positive voltage from V2 is applied the buffer reservoir electrode 30 by closing S2. S1 is open in this mode, allowing current to flow through the ammeter to ground. The detector 18 and detector 20 reservoirs are held at ground potential as in the sample loading mode. Diode D3 is reverse biased and D1 is forward biased placing resistors R3 and R1 in series with the ammeter circuits.

The resulting electroosmotic flow moves fluid from the 14(b) channel into the 14(a), 12(a) and 12(b) (left hand side) channel legs. The analyte sample introduced into the channel intersections 40 and 42 in the loading mode is moved into the 14(a) channel where separation occurs. The electric field across 14(a) is determined by the applied voltage V1, length and cross-sectional geometry of 12(a) and 12(b) (left hand side), as well as the values of resistors R1 and R3. The resistors R1 and R3 reduce the field in the 12(a) and 12(b) channels by limiting the current that can flow in these channel legs and therefore reducing the flow in these channel legs as well.

Figure 4:
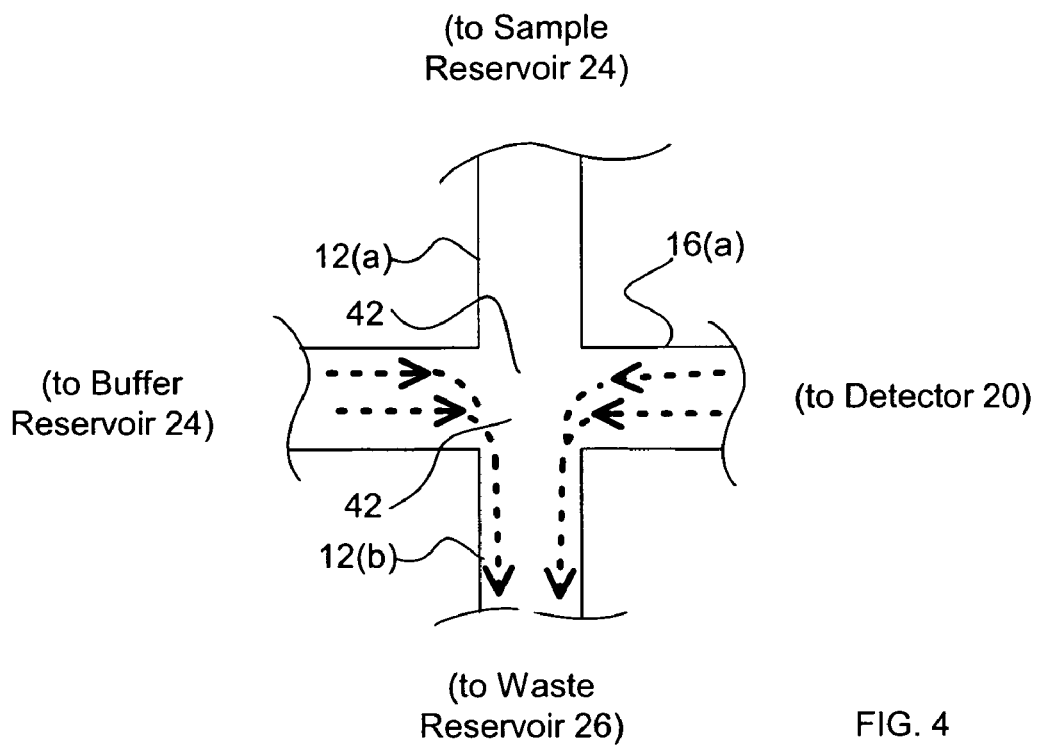
FIG. 4 is a schematic of a portion of the example capillary electrophoresis system of FIG. 1 illustrating sample and buffer solution at the end of a sample loading mode.
Figure 5:
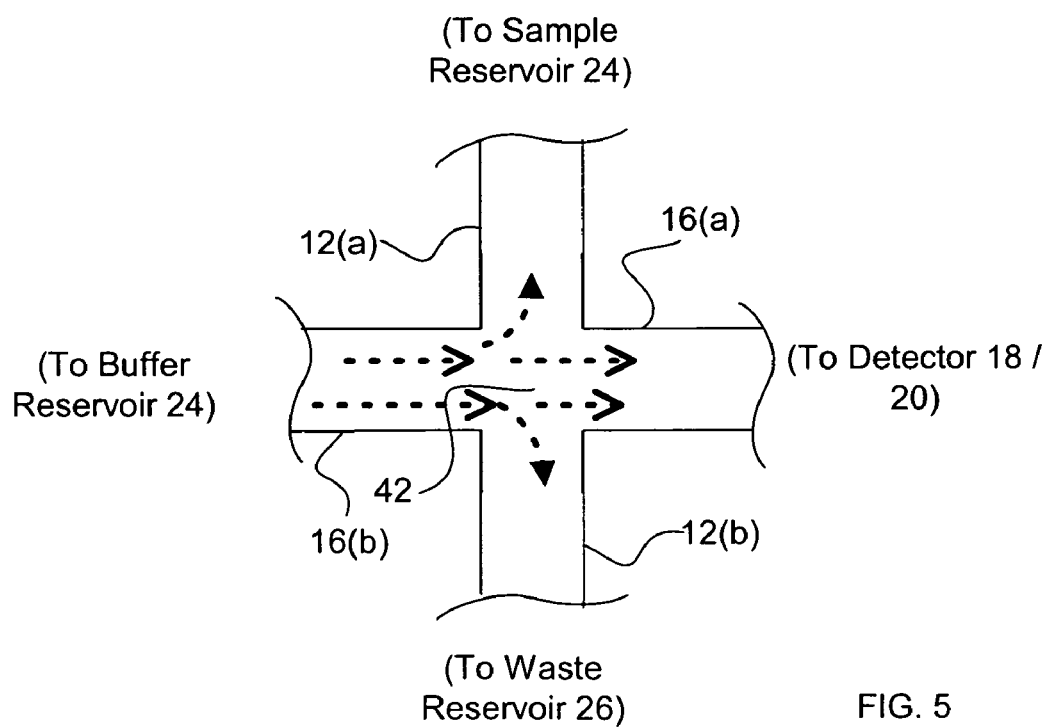
FIG. 5 is a schematic of a portion of the example capillary electrophoresis system of FIG. 1 illustrating sample and buffer solution during operation of a driving circuit.

It will be appreciated that the schematics of FIGS. 2 and 3 are illustrative only. In practice, analyte migration during loading and separation may be somewhat more complex than as schematically illustrated in FIGS. 2 and 3. FIGS. 4 and 5 have been provided to provide what may be a more accurate representation of analyte migration during some sample loading and separation operations of systems of the invention.

FIGS. 4 and 5 show the region about intersection region 42 of FIGS. 2 and 3 that have been circled in dashed line, including portions of the loading micro channel 12 and of the separation micro channel 16. It will be appreciated that FIGS. 4 and 5 are likewise useful to illustrate the intersection 40 which may be undergoing substantially the same migration effects as intersection 42. FIG. 4 shows the intersection 42 during the loading mode. As shown, the channel leg 12(*b*) may be filled with some combination of sample and buffer solution (represented by dashed line) as the electric field between generated by the loading circuit draws some buffer solution to migrate towards the waste reservoir 26.

FIG. 5 shows the intersection region 42 and surrounding area of FIG. 3 after an electric field generated by the driving circuit has caused some buffer solution to migrate towards both the sample reservoir 24 and waste reservoir 26 (which are grounded) and causes a highly discrete and symmetric sample plug to migrate towards the detector system 20.

As used herein, the term "symmetrical plug" is intended to be broadly interpreted as referring to a well defined geometric (and hence volumetric) shape. One example is a generally triangular plug resulting in the vertex (on the 12(*b*) side) being in the middle of the intersection 42 along its width. If the flow from the sides (16(*a*) and (*b*)) are minimized while still "containing" the sample stream, the plug would approach a square. Containing the sample stream is desirable since if it were allowed to freely diffuse from the intersection 42 into the channels 16(*a*)-(*b*), the volume of sample would be difficult to determine. By substantially containing the sample stream in the intersections 40 and 42 and measuring the channel currents (which are proportional to flow), the volume of a sample plug can be approximated.

Some example systems of the invention may include means for measuring current along any of the channels 12, 14 or 16, with an example being an ammeter. An ammeter may be placed, for example, in contact with each of the legs 12(*a*)-(*b*), 14(*a*)-(*b*), and 16(*a*)-(*b*) to measure the current therein. The ammeters can be connected to and controlled by the controller 58.

Tests may be run in differing amounts of time depending on particular system 10 configuration, including size of the channels, electric fields generated, and the like. In many systems of the invention, typical tests may take about 3-5 minutes. Between tests, all of the channels (and reservoirs) may be flushed with buffer solution if desired, or with other solutions such as a NaOH solution, to remove sample residue. Also, in some example embodiments, it may be useful to pull vacuum from one or more of the reservoirs (with examples being just the waste reservoir or from all reservoirs) to clear all microchannels of sample, buffer, and sample-buffer mixture. Combinations of sequential flushing and vacuum may be used to ensure that substantially all traces of sample have been removed. One or more rinses with deionized water may also be performed.

Other example structures of the invention can similarly deliver a discrete and symmetric sample plug through other means. For example, other capillary electrophoresis systems of the invention contemplate use of one or more valves or one or more pneumatic drivers (such as a pump, compressor or pressurized source), or gravity. While these alternatives may find utility in some embodiments of the invention, in the present example illustrated in FIGS. 1-5 portability and miniaturization is desired. In such circumstances, it has been discovered that the configuration of FIGS. 1-5 offers advantages. Addition of pumps, valves, or the like would add complexity, weight, and bulk to the example capillary electrophoresis system 10.

Also, while some example capillary electrophoresis systems of the invention contemplate use of pneumatic devices and/or valves, in some applications use of these elements may not be desirable. These elements, with pumps and valves being two examples, carry a risk of introducing fluid flow perturbations that can be disadvantageous to testing, with examples being disruption to separation and detection.

Figure 6:
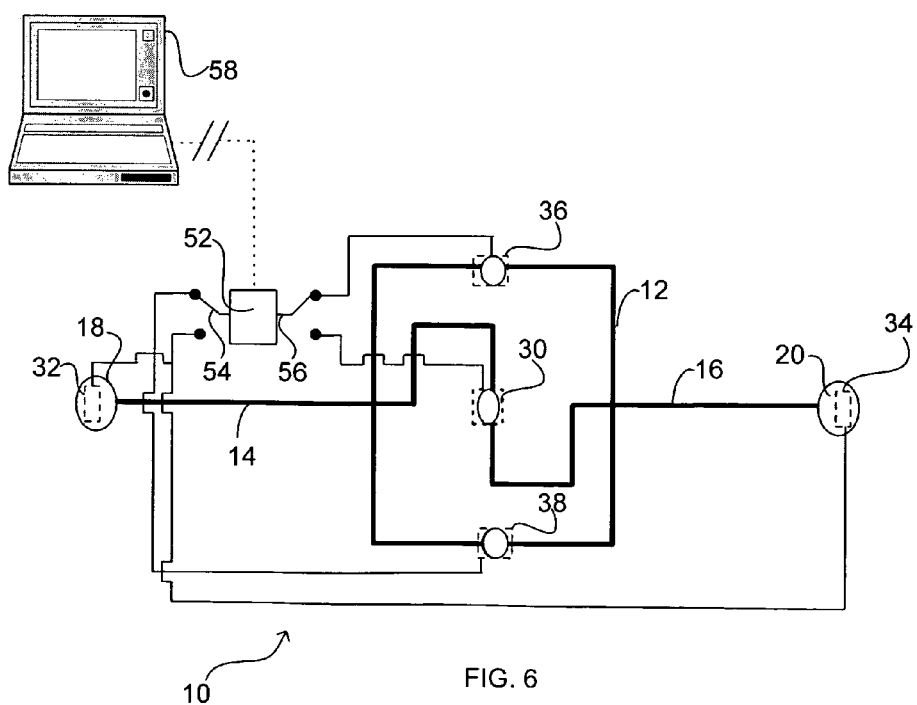
FIG. 6 is a schematic of the example capillary electrophoresis system of FIG. 1 illustrating power supply.

FIG. 6 is useful to additionally illustrate example power supply and circuitry aspects of the example system 10. The simplified schematic of FIG. 6 illustrates an additional element of the example capillary electrophoresis system 10 that has been discovered to be useful to compact and miniaturized scale system: a common power supply 52 used to apply a potential across both the driver circuit electrodes 30, 32 and 34 in addition to the loading circuit electrodes 36 and 38. The power supply 52 may be considered to be, for example, voltages V1 and V2 of FIGS. 2-3.

Although some example systems contemplate use of an AC power supply, the typical power supply 52 is a DC power supply, and in many portable and miniaturized applications is a low voltage DC power supply. The power supply 52 is a single, dual source (both positive and negative voltages provided). A dual source power supply 52 is useful to eliminate the need for a separate power supply at each reservoir, as well as for other reasons. The power supply 52 may include a DC battery(s) which might be disposable or rechargeable. By way of particular example, in one example system of the invention the power supply 52 included 4 1.5V AA-size rechargeable batteries. A continuous operating life time of about 15 hrs was provided, and a maximum DC voltage of about ±1.2 kV was provided.

The simplified schematic of FIG. 6 illustrates two switches 54 and 56 in electrical communication with the power supply 52 that may be placed in a first position to apply two parallel potentials across the driver circuit electrodes 30-32 and 30-34 (driver circuit), and placed in a second position to apply a potential across the loading circuit electrodes 36-38 (loading circuit). No standby position is provided (where no circuit is being powered), although other example systems of the invention may include a standby configuration. An on/off switch may also be provided.

While other example systems of the invention utilize separate power supplies for each of the driver and loading circuits, use of a single power supply 52 in the manner shown has been discovered to offer advantages related to low bulk, weight, and the like as well as eliminating electrical bias effects between power supplies and other electrical components. These advantages are desirable when practicing an invention embodiment where portability is desirable.

The switches 54 and 56 are illustrative only. A variety of switch mechanisms may be used in practice of the invention. For this reason, use of the term "switch mechanism" herein is intended to be broadly interpreted, and is not limited to any number of switches or any particular switch structure. On a miniaturized scale, for example, a switch mechanism, such as the switches 54 and 56, will not likely be mechanical but instead may be micro electronics switch elements, including but not limited to logic gates, transistors, integrated circuit components, and the like.

It will be appreciated that the simplified schematic of FIG. 6 is illustrative only, and that other elements may be included. For example, the power supply 52 might further supply the detector systems 18 and/or 20. In other embodiments, detector systems 18 and 20 utilize one or more dedicated power supplies, with one example being a 9V battery provided for powering both detector systems 18 and 20.

FIG. 6 also illustrates a controller 58 electrically linked to the power supply 52 and to the switches 54 and 56. The controller may be used to control the power supply 52, the switches 54 and 56, and other components of the system 10. As shown in FIG. 1, for example, the controller 58 may also be connected to the detector systems 18 and 20 to control them and to record data output by them. It will be appreciated that the controller 58 may likewise be connected to other elements of the capillary electrophoresis system 10, but such connections have been omitted from various FIGS. for convenience. The controller 58 has been illustrated as a laptop computer, but it will be appreciated that the controller may likewise be a benchtop computer, another processor based device, an electronic device, micro-circuitry embedded on a chip, or the like.

Also, the connections to the controller 58 have been illustrated in FIGS. 1 and 6 with a break in the connection line to indicate that the controller 58 may be located separately from the other components of the capillary electrophoresis system 10. This may be the case, for instance, when the system 10 is miniaturized and is contained on a micro chip and the controller is external to the chip, with an example being an external computer for interfacing with the chip based system 10. The controller may include one or more software programs stored in a memory and useful to control the power supply 52, switches 54 and 56, detector systems 18 and 20, and other components. The controller may also have one or more software programs for processing data, storing data in a memory and providing graphical format output. A graphical user interface may likewise be provided for operating the controller 58 and the components it is connected to.

In some example capillary electrophoresis systems of the invention that are fabricated on a chip on a miniature or micro-scale, for example, the controller 58 may comprise logic circuitry that is embedded in the chip. Or, the controller 58 may comprise a commercially available plug-in chip or circuit board that interfaces with the CE system chip.

As best illustrated by the schematic of FIG. 3, the sample plug 50 including analytes migrating at different rates continue migrating along the micro-channels 14 and 16 towards the micro-channel ends 44 and 46 and the detector systems 18 and 20 that are proximate thereto. As the analytes 48 and 50 pass into a detection zone the detector systems 18 and 20 may detect and identify them. A wide variety of different detector systems can be used with capillary electrophoresis systems of the invention. These include, for example, optical detectors such as ultraviolet (UV) detectors, fluorescence detectors, electrochemical detectors and mass spectrometer detectors. The example capillary electrophoresis system 10 utilizes electrochemical detector systems 18 and 20.

Electrochemical detectors are generally known in the art, and a detailed description is therefore not necessary herein and will not be provided for sake of brevity. By way of brief summary, example electrochemical detector systems 18-20 of the invention may include two or three electrodes. With a three electrode detector, the electrodes can be referred to as work, reference and auxiliary. The work electrode(s) can comprise a single or multiple electrodes in the detection reservoir. A constant voltage is applied between the work and reference electrodes, which causes a constant base current to flow through these two electrodes. When an analyte travels over the work electrode, the charge on the analyte causes it to participate in an oxidation/reduction reaction with the work electrode. The electrons gained or lost by the work electrode cause an increase or decrease in current, which is quantified by a component of controller 58, and indicates the presence of an analyte flowing through the micro-channel and quantifies the same.

Figure 7:
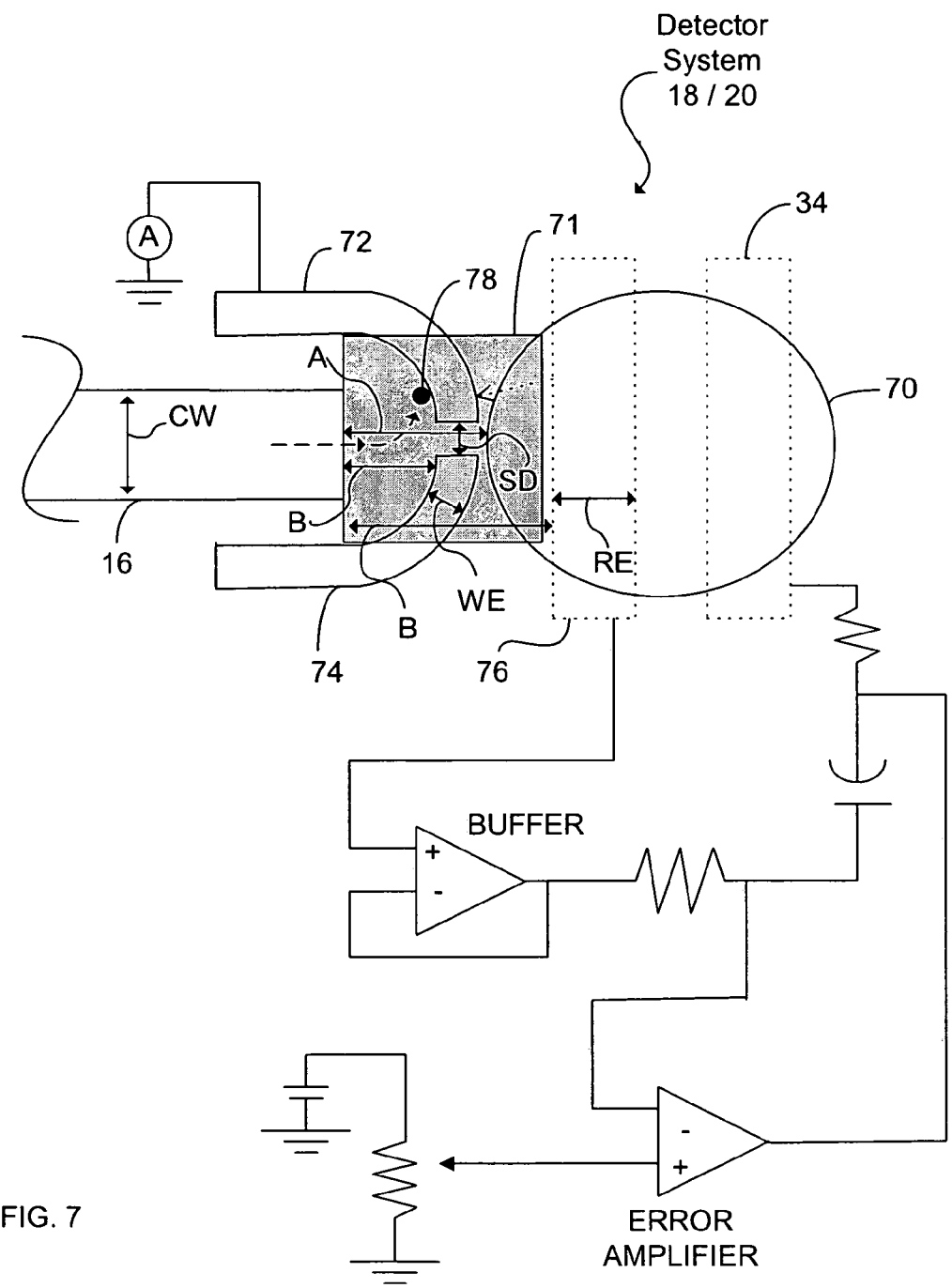
FIG. 7 is a schematic of example detection electrodes of the capillary electrophoresis system of FIG. 1.

Having now presented a brief description of principles of operation of the detector systems 18 and 20, more detailed discussion of their configuration can be made. FIG. 7 is a schematic of one example configuration for an example detector system 18 or 20 useful with capillary electrophoresis systems of the invention, including a detection reservoir 70. The separation micro-channel 16 communicates with the reservoir 70, both of which are filled with a conductive buffer solution. A shelf area 71 delivers fluid from the channel 16 to the reservoir 70. The shelf area 71 may comprises an etched portion of a substrate. The shelf area 71 and the reservoir 70 are each wider than the channel 16. The shelf area 71 has been illustrated in gray-shade for clarity in FIG. 7.

The example detector systems 18 and 20 include three electrodes: a first work electrode 72, a second work electrode 74, and a reference electrode 76. As will be appreciated by those knowledgeable in the art, the detector system may further include an additional auxiliary or counter electrode. One is not shown in FIG. 7, however, since in the example detector system the functionality of this electrode has been combined with the cathode electrode 34. Reference electrode 76 and cathode 34 have been shown in dashed to indicate that they may be located below the reservoir 70 in a stacked, vertical configuration, or may comprise thin conductor layers deposited at the floor of the reservoir 70. FIG. 7 shows the work electrodes 72 and 74 outside of the reservoir 70 in the shelf area 71. In some invention embodiments, these electrodes may be positioned within the reservoir 70.

As the analytes exit the channel 16, they enter the shelf area 71. Because the shelf area 71 and the reservoir 70 are wider than the channel 16, a volume of fluid leaving the channel 16 will have a lesser depth in the shelf area 71 and reservoir 70 (i.e., the same volume of fluid rises to a greater height in the narrower channel 16 than in the wider shelf area 71 or reservoir 70). This is useful to confine the analyte ions as low and close to the work electrode 72/74 (which may be thin conductors along or forming a portion of the shelf area 71 or reservoir 70 floor) as possible as they go past them for better detection sensitivity. Also, if the reservoir 70 is drilled in a substrate, it may be desirable to separate this from the channel 16 by some distance to avoid damage of the channel 16 through the drilling process.

A power supply (not shown) and a controller (such as controller 58 of FIG. 1) may also be provided. The electrodes 72, 74 and 76, as well as a power supply may be considered to be collectively represented by the detector system 18 and 20 elements shown in FIGS. 1-4 (illustrated as circles). Also not shown in FIG. 7 are electrical connections to the electrodes 72-76 and a controller (such as controller 58, FIG. 1). These and other components may be included in the electrochemical detectors of the invention. These components and their operation, however, are generally known in the art and description herein is therefore not necessary.

One of the work electrodes 72 or 74 is typically connected to ground through an ammeter circuit, with the other functioning as a redundant testing electrode and can be left "floating" (not connected to ground) if not used as the working electrode in another potentiostat circuit. FIG. 7 shows electrode 72 connected to ground. A low-voltage (0.4 V-1.2 V) is applied to the circuit to force the solution to a certain potential which is measured by the reference electrode 76. The reference electrode helps to control and maintain the voltage across 72 and 74. When a sample analyte comes in contact with the work electrode 72, either oxidation or reduction occurs. The gain or loss of electrons in the sample causes a current in the buffer solution across the electrodes 72 and 74.

The detector reservoir 70 may use a potentiostat to set the potential of the conductive buffer solution versus the working electrode 72 or 74. The work electrode 72 is held at ground potential using a transimpedance amplifier (Ammeter circuit—current to voltage converter). When an analyte 78 exits the micro-channel 16 as it migrates due to the electric field exerted by the driver circuit towards the reservoir 70, it encounters the applied potential from the work electrode 72 in a detection zone and undergoes either a reduction/oxidation reaction.

When such an oxidation/reduction occurs, current flowing through this part of the circuit is measured and is the detection signal that can be used to identify the analyte 78. The solution is pulled negative relative to ground for cases when a positive work electrode potential is desired (a positive electrode potential is required for oxidation, while a negative electrode potential is required for reduction). The reference electrode 76 is buffered by a high input impedance amplifier and monitors the potential of the buffer solution. This potential indirectly adjusts the error amplifier which provides voltage to the auxiliary electrode 34. The voltage drop across a series resistor (R4) placed between the error amplifier and auxiliary electrode is measured to determine the current flowing into the electrode. This measured current is used as channel current and indicates magnitude of flow in the separation channel.

As illustrated, cathode 34 is downstream from the detector electrodes 72-76. Typically the detector circuitry is separate from the remaining capillary electrophoresis system 10 circuitry. The capillary electrophoresis electrical field is established to cause migration of analyte and buffer ions through the micro-channels of the system 10. The detector 18 and 20 voltages establish a very small voltage in the detection zone that is adequate to initiate oxidation/reduction when an electroactive analyte enters the detection region.

Use of the term "detection zone" herein is intended to broadly encompass a region where a detector can detect and/or identify an analyte. In the example detector configuration of FIG. 7, the detection zone may be considered to be the reservoir 70 or a region proximate thereto. In other example capillary electrophoresis systems of the invention which utilize other detectors, the detection zone may differ depending on the detector used. For example, in-channel detection may be used. An optical detector in another example capillary electrophoresis system of the invention may utilize a transparent or translucent portion of the separation micro-channels 14 and 16 to define a detection zone proximate to the micro-channel end 46. Or, a reservoir similar to that shown in FIG. 7 could be utilized with an optical detector. Likewise, other detectors may utilize different detection zones which may be located on or in the separation channel, the detector reservoir, or regions adjacent thereto.

Choice of detection technology and configuration of the detector zone will vary with application design and like parameters, as will the scale of the detection zone and detector components will likewise. It will be understood that FIG. 7 (as well as other FIGS. discussed herein) has not been drawn to scale. By way of illustration of one example configuration only, the detector and detection zone illustrated in FIG. 5 included the following dimensions:

Channel width (CW)=about 50 micron
Work Elect. Width (WE)=about 40 micron
Distance from Channel Exit to Reservoir (A)=about 1 mm
Ref. Electrode Width (RE)=about 1 mm
Work Electrode Separation Distance (SD)=about 20 micron
Distance from Channel Exit to Reference Electrode (B)=about 50 micron Although a variety of detectors are suitable for use with capillary electrophoresis systems of the invention, it has been discovered that electrochemical detector systems offer useful advantages and benefits related to size, weight, simplicity of circuitry, and the like that are well suited to highly portable and miniaturized applications. For example, in some miniaturized applications, electrochemical detector systems can offer advantages over absorbance or fluorescence detectors in ease of fabrication, simpler electronics, portability as well as ease of use.

It will be appreciated that although an example system 10, its components, and its operation have been described herein, such description is illustrative of only an example embodiment of the invention with many other configurations and components suitable for practice of the invention. For example, the channels 12(*a*)-(*b*), 14(*a*)-(*b*) and 16(*a*)-(*b*) have been described as having substantially equal lengths to achieve equal electrical resistance. Other configurations can also be utilized to achieve equal resistances over the legs 12(*a*)-(*b*), 14(*a*)-(*b*) and 16(*a*)-(*b*).

Figure 8:
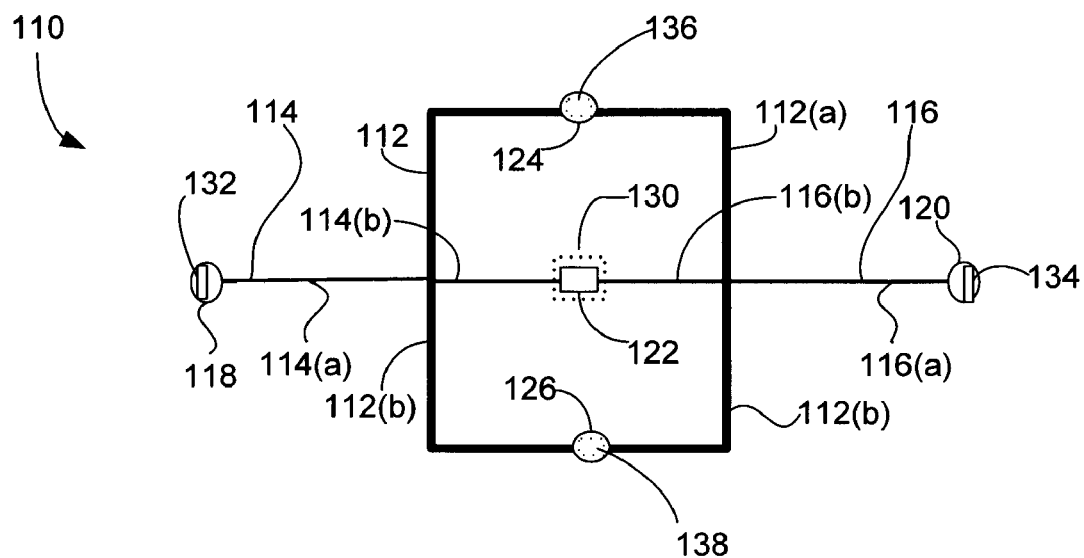
FIG. 8 is a schematic of a second example capillary electrophoresis system.

For example, one of the legs 12(*a*)-(*b*), 14(*a*)-(*b*) and 16(*a*)-(*b*) may have a shorter length but a narrower cross section (i.e., "high" resistance per unit length) to result in the same electrical resistance as a longer leg with a wider cross section (i.e., "low" resistance per unit length). Such a configuration has been schematically illustrated in the example capillary electrophoresis system 110 of FIG. 8. The system 110 is generally consistent with the system 10, and like element numbers have been used in a 100 series for clarity. In the example system 110', the legs 114(*b*) and 116(*b*) have a shorter length but a narrower cross section than the longer legs 112(*a*) and 112(*b*) which have larger cross section dimensions (difference in channel diameters is illustrated in FIG. 8 through thickness of lines).

The result of these variations is that the resistance over the legs 112(*a*)-(*b*) is substantially equal to that of legs 114(*b*) and 116(*b*). In this manner, the present invention contemplates varying separation micro-channel and/or loading micro-channel length, cross section, and other dimensions as may be desired to achieve substantially equal electrical resistance.

Many other modifications to the example capillary electrophoresis systems 10 of FIGS. 1-7 may also be made. Although only two separation micro-channels 2 have been illustrated, other embodiments may include three, four, or any larger number that may be practical. For example, other example systems of the invention may include generally rectangular, oval, circular or other shaped loading micro-channels 12 with 4, 6, 8 or other numbers of separation channels extending therefrom in a hub-and-spoke configuration. Other shapes of the micro-channel 12, 14 and 16 are possible, including nonlinear shapes.

Greater numbers of channels may require larger power supplies to cause current to flow through the additional channels. A highly miniaturized system, however, is useful to reduce power consumption even with multiple channel configurations. In the example system 10, the driver circuit can provide about 1000 V at about 1 mA. At 250 V, typical currents are in the range of 10 micro amps. Accordingly, it is well within the operation of the current power supply to provide the necessary CE field for many dozens of micro-channels. By way of comparison with larger systems, benchtop power supplies are applying voltage across discrete capillaries that are many centimeters long and therefore require many 1000's of volts to establish fields in the range of 100-200 V/cm. But as long as the buffer concentration and cross sectional areas of the discrete capillaries are similar to the microchannels, the currents are only in uA range. This is one reason that smaller chip-based systems such as the example system 10 may be advantageous for some applications, with an example being multiple channel applications where relatively small power supplies are desired.

The number of separation micro-channels used in a particular embodiment of the invention, in addition to other design variables of capillary electrophoresis systems of the invention, will depend at least to some extent on the particular application that embodiment is intended for. For example, some capillary electrophoresis systems of the invention will be useful for performing redundant testing on a sample. In such applications, two or three separation micro-channels may be suitable.

The capillary electrophoresis system 10 of FIG. 1, by way of example, can be used to achieve through a single test run redundant analysis of a sample. Supply of a single sample to the sample reservoir 24 and operation of the system 10 as described above will result in the testing of identical sample material in each of the separation micro-channels 14 and 16. If the detector systems 18 and 20 are configured to perform identical detection, they will provide redundant test results on the sample. Using single channel capillary electrophoresis systems of the prior art would require two separate test runs, with the associated risk that some contamination or inconsistency between samples might occur between tests.

In addition to being useful to quickly perform redundant testing, example capillary electrophoresis systems of the invention may be used to provide other test results. With reference to the CE system 10 of FIG. 1 again made by way of example, the two detector systems 18 and 20 could be configured to perform different detection. This may be useful, for instance, when a single sample may contain two analytes that are difficult to detect with a single detector. When using a single capillary electrophoresis system of the prior art, for example, it may be difficult or impossible to detect two analytes that had identical (or very similar) electrophoretic mobilities, since they could effectively mask one another. In the example system 10 of the invention, however, this situation could be effectively addressed by configuring the detector system 18 to detect a first analyte and configuring the detector system 20 to detect a second analyte (that might, but does not necessarily, have the same electrophoretic mobility as the first analyte).

Accordingly, it will be appreciated that use of identical detector systems 18 and 20 may be desirable for some testing applications, while use of different detector systems 18 and 20 may be desirable for others. Some example capillary electrophoresis systems of the invention may vary between these two applications. In a multiple separation channel system of the invention that has more than two detectors, for example, some portion of the detectors may be identical and some may be different—a capillary electrophoresis system that includes four detector systems may have two "type X" detectors and two "type Y" detectors. This will allow for a single sample to be subjected to redundant testing for both the "X" analyte (detectable by "type X" detector) and the "Y" analyte (detectable by "type Y" detector).

As discussed above, a variety of different detectors are suitable for use with the invention. Each different type of detector may be configurable to detect some particular analyte in some manner. Taking electrochemical detectors by way of example, one or more of the electrodes of one or more of the detectors may be functionalized to allow it to detect different analytes. Different materials of construction may be used for one or more of the electrodes, with Pt, Au, and C being examples. Different catalyst layers on the electrode(s) may also be used, with examples including precious metal and polymer based catalyst layers. For example, the electrodes can be coated with polypyrrole which then each can be activated with an enzyme specific for a certain sugar (e.g., glucose oxidase on one electrode, fructose oxidase on another, etc.). A mixture of sugars could be analyzed whereby each electrode would specifically detect the sugars associated with the attached enzyme.

Another design consideration in fabricating capillary electrophoresis systems of the invention relates to scale. Although multiple capillary electrophoresis systems of the invention will offer useful benefits and advantages on a number of different scales, including but not limited to laboratory bench scale, the example capillary electrophoresis systems illustrated schematically in FIGS. 1-6 may be particularly well suited to a micro-scale. For such systems, embodiments of the present invention are contemplated to be substantially contained on a micro-chip.

The chip may be a substrate typically used in fabrication processes, with examples including a silicon based chip, a glass based chip, a soda-lime glass based chip, or a polymer based chip, with examples including Mylar D polyethyleneterephthalate (PET), polymethyl methacrylate (PMMA), poly(dimethylsiloxane) (PDMS), polycarbonate (PC) and polyethyleneterephthalate glycol (PETg). The chip may be layered, and/or fabricated using etching and deposition techniques that are well known in the art and need not be discussed herein.

When an electrophoresis system of the invention such as the system 10 is contained on a chip, the micro-channels 12, 14 and 16 may comprise substantially rectangular (or relative closely approximated shaped) channels that have been formed through etching, deposition and/or other known chip fabrication techniques. The size of the channels may vary according to application and other design parameters.

By way of example only, suitable channel cross sectional widths and heights may be of the order of 10-100 microns. Cross sectional areas are generally on the order of about 50-60 micron wide by about 20 micron deep—discrete silica capillaries have diameters on the order of 25-50 micron. Channel lengths should generally be longer for lower separation voltages, or shorter when large voltages are used. These factors are determined by (and directly affect) analytical chemistry phenomena such as separation efficiency and resolution. Large voltages and small cross-sectional areas can be problematic due to Joule heating, which can heat up the channel and denature proteins or DNA (if biological samples are being investigated). Also, as channel cross-sectional areas get smaller, interfacing with the "outside world" becomes more of an issue, with examples being sample loading and system flushing/cleaning. It is believed that systems of the invention will be useful with micro-channel widths of as small as about 5 microns.

Those knowledgeable in the art will appreciate that chemical analysis systems when micro-fabricated on a micro-scale and placed on a micro-chip may be referred to as a "lab-on-a-chip" (LOC), as a "micro total analysis system" (micro-TAS), or using other like terms known in the art. It will be appreciated that some example systems of the invention, when practiced on a micro-scale, may be accurately described using these general terms, with an example being that a system of the invention may be a LOC.

Figure 9:
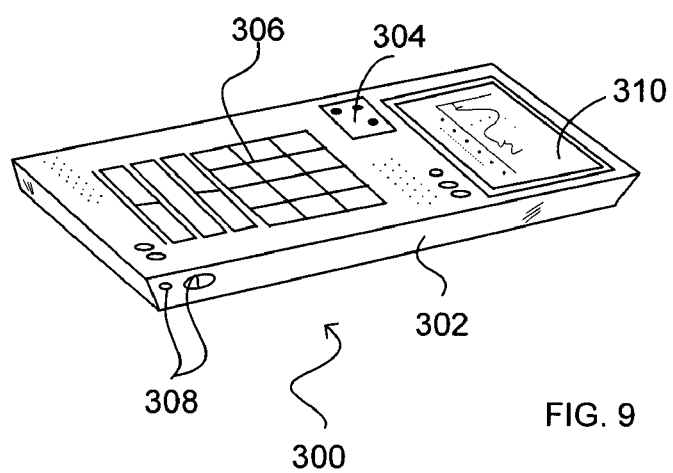
FIG. 9 illustrates an example handheld capillary electrophoresis system.

In one particular example embodiment of the invention, one or more capillary electrophoresis systems of the invention, with an example being that schematically illustrated in FIGS. 1-7, is placed on one or more chips that are held in a handheld electronics housing. FIG. 9 illustrates an exemplary handheld system 300. The system 300 may include a small handheld housing 302 which might be, for example, the size of a small handheld calculator, small PDA, or even a credit card. The example system 300 includes one or more fluid communication ports 304 for injecting sample (using a hypodermic syringe, for example), buffer, flushing solution, and removing waste. These ports 304 may communicate with, for example, the sample reservoir 24, buffer reservoir 22, and waste reservoir 26 of FIG. 1. These ports may be configured to cooperate with a micro-liter syringe or other suitable transfer device for loading of sample, buffer, and removal of waste.

The system 300 further includes data entry means such as keys or buttons 306 for entering data and controlling test operation. Other data entry means are contemplated, with an example being a touch screen. Communication ports 308 are configured for electronic interface with other devices such as other computers, laboratory devices, data storage devices, and the like. The ports 308 could likewise interface with an external computer that could be used to control tests and capture output data. One or more memories for storing digital data may further be provided in the housing 302. A screen 310 is provided for displaying data and information useful to perform tests.

One or more chips within the cabinet may include a capillary electrophoresis system circuit as schematically illustrated in any of FIGS. 1-8, including all of their elements (reservoirs, channels, detectors, power supply(s), etc.). If the example handheld capillary electrophoresis system 300 contains multiple individual chips (each containing a multiple separation micro-channel CE system), the housing 302 might further describe these chips as an "A" multi-channel capillary electrophoresis system, a "B" multi-channel capillary electrophoresis system, a "C" multi-channel capillary electrophoresis system, etc. Each of the A, B and C systems can be equipped with different detectors suitable for identifying different analytes. This would result in a single, portable system 300 that was suitable for redundant testing to identify multiple different analytes. A highly portable capillary electrophoresis system 300 will be useful for a variety of applications that put a premium on portability, with examples including bedside medical testing, field environmental testing, homeland defense testing applications, and the like.

Other example embodiments of the invention include miniaturized disposable, single-use capillary electrophoresis systems. One or more systems as illustrated in FIGS. 1-8 might be contained on a chip intended for a single use. Following use, the system might be disposed. This could be combined with a handheld system such as system 300 illustrated in FIG. 9 whereby the handheld cabinet was configured to removably receive chips having a capillary electrophoresis system such as that illustrated in FIG. 1 thereon. The cabinet 302 might include the detector systems, controller and selected other components for interfacing with micro channels and reservoirs of the system 10.

In order to further illustrate example embodiments of the invention, several example systems of the invention, example test runs, and example data obtained through methods of the invention and use of systems of the invention shall be provided.

Example Methods and Results

In one example LOC capillary electrophoresis system, a soda-lime glass-based electrophoresis system of the invention generally consistent with that illustrated in FIG. 1 was fabricated using traditional microtechnology processes, including UV photolithography, buffered oxide etch (BOE), electrode deposition and compression thermal bonding. The example system was characterized with a mixture of dopamine (2 mM) and catechol (2 mM) in a phosphate buffer (20 mM, 6.5 pH). Modeling results yielded migration velocities of 0.6 mm/s and 0.42 mm/s for dopamine (electrokinetic (EK) mobility=60,000 $\mu m^2$/V-s) and catechol (EK mobility=42,000 $\mu m^2$/V-s), respectively. Experimental results obtained from microchips of the invention exhibiting the same EK mobilities demonstrated identical electropherograms in both separation micro-channels 14 and 16 with migration velocities of 0.58 mm/s for dopamine and 0.41 mm/s for catechol.

Computational Modeling

Several alternate designs with varying geometries were constructed and analyzed using finite element software. In the computational modeling studies, the geometry presented in FIG. 1 was most successful in introducing substantially equal volumes of sample into the intersections 40 and 42 and generating suitably low sample plug distortion. The final design resulted in a channel width of about 50 $\mu m$ (for all micro-channels 12, 14 and 16), and an equidistant length of about 750 $\mu m$ from the intersections 40 and 42 to the sample reservoir 24, waste reservoir 26, buffer reservoir 26 and detector systems 18 and 20 to obtain balanced currents in all the micro-channels 12, 14, and 16.

The boundary conditions used in the computational model solver were:
applied injection voltage=30V
separation voltage=15V
resultant an electric field of 100 V/cm;
dopamine EK mobility of 60,000 $\mu m^2$/V-s (empirically determined)
catechol EK mobility of 42,000 $\mu m^2$/V-s (empirically determined)

Even though the above values of EK mobility were used, the observed EK mobilities obtained from the migration velocities of dopamine and catechol were 30,000 $\mu m^2$/V-s and 20,830 $\mu m^2$/V-s, respectively. The specified EK mobilities were halved because the finite element model is solved in a constant-current mode, whereas the electronics used for the LOC data acquisition were based on constant-voltage mode.

Example Electrophoresis System Fabrication

The channels 12, 14 and 16 may comprise micro channels etched or otherwise formed on a miniature scale in a substrate. In the fabrication of one example system 10, a first substrate is patterned on a first surface with the channels 12, 14 and 16 though etching or other known techniques. Reservoirs 22, 24 and 26 may be substantially cylindrical shaped voids drilled or otherwise formed extending completely through the first substrate and in communication with the channels at desired locations. A separate blank substrate (electrode substrate) is then deposited and patterned with metal layer to form the electrodes in desired dimensions and locations. This electrode substrate is then bonded vertically with the channel substrate, with the electrodes facing the first surface of the channel substrate so that the electrodes and the channel/reservoirs face each other. In this manner the channels are "sealed" about their perimeters, the electrodes deposited on the electrode reservoir form a portion of the wetted floor of the reservoirs, and the reservoirs are accessible for introducing or removing fluids to the channels.

The final design/pattern was created as an L-Edit file and two masks were fabricated using a laser pattern generator. The LOC electrophoresis system of the invention was constructed from two unexposed photomask blanks (10 cm×10 cm) that were comprised of ultra-flat soda lime glass precoated with a low reflective chrome and positive resist. The micro-channels (generally consistent with micro-channels 12, 14 and 16 of FIG. 1) were photolithographically patterned in a top glass substrate and formed using BOE. The reservoirs (D=5 mm) (consistent with sample, buffer, waste and detector reservoirs 22, 24 and 26) were created using a diamond-tipped drill bit mounted in an ultra-high-precision micromilling machine.

The bottom substrate, consisting of both the capillary electrophoresis system and electrochemical detector electrodes, was photolithographically patterned, etched 300 nm using BOE, DC sputtered with Pt and patterned by a lift-off process. The electrodes were recessed in order to insure a better glass-to-glass bond during the thermal compression bonding step (T=625° C. for 2.5 hrs.).

Figure 10:
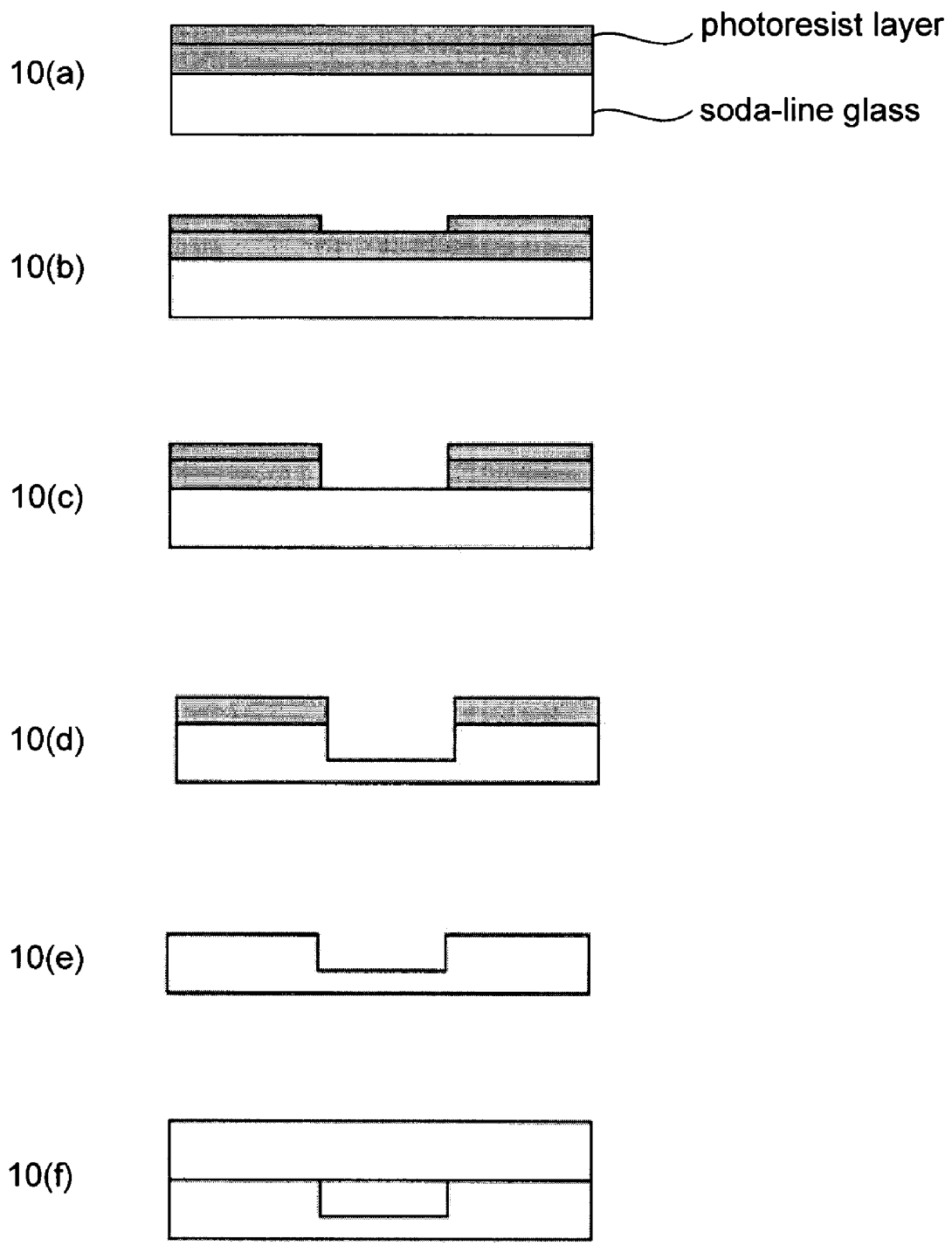
FIG. 10 is useful to illustrate a method for fabricating an example system of the invention.

FIG. 10 graphically illustrates stages involved in fabricating a microchip. A soda-lime glass based substrate was obtained from Nanofilm, Inc. (California) (step 10A). Patterning was then performed to remove a portion of a top photoresist layer (step 10(b)). Chrome etching then removed a coincident portion of a lower level (step 10(c)). Glass etching is then performed in BOE to further define a channel (step 10(d)). Chrome etching is then performed (step 10(e)). A step of drilling the substrate from its bottom surface may also be performed to form reservoirs in communication with the channels in desired locations. Finally, a top substrate layer is attached to define a channel (step 10(f)). As described above, electrodes may have been deposited in the top substrate layer at desired positions so that they are exposed to the reservoirs.

Experimental Details and Results

Each chip was tested and evaluated for performance. A mixture of dopamine (4 mM) and catechol (4 mM) in a phosphate buffer solution (20 mM, pH 6.5) was used for evaluating chip performance with a sample loading voltage of 250 V. Separation voltages ranged between 240 V and 500 V, while the applied ECD reference voltage ranged between 0.3 V and 1 V.

A total of 4 dual CE-ECD LOC platforms were fabricated and tested, with the following dimensions:

| | |
|---|---|
| Length of separation channel | 18 mm |
| Length of injection channel | 18 mm |
| Channel Width | 50 µm |
| Distance between channel exit and detection electrodes | 50 µm |
| Width of detection (work) electrode | 40 µm |

Although the separation channel length of the computational model was a few orders of magnitude smaller than that of the fabricated CE microchip (to reduce simulation run time), the migration velocities obtained from either could be compared because EK mobilities and applied separation electric fields were the same.

A computer model found the velocity of dopamine to be 0.06 cm/s and catechol to be 0.042 cm/s for a separation electric field of 100 V/cm, whereas a dopamine velocity of 0.058 cm/s and catechol velocity of 0.041 cm/s were obtained in the experimental studies for a separation electric field of 97 V/cm. Nearly identical separation and detection of dopamine and catechol were clearly demonstrated in each of two microchip capillary electrophoresis systems of the invention as shown in the resultant data of FIG. 10.

Figure 11:
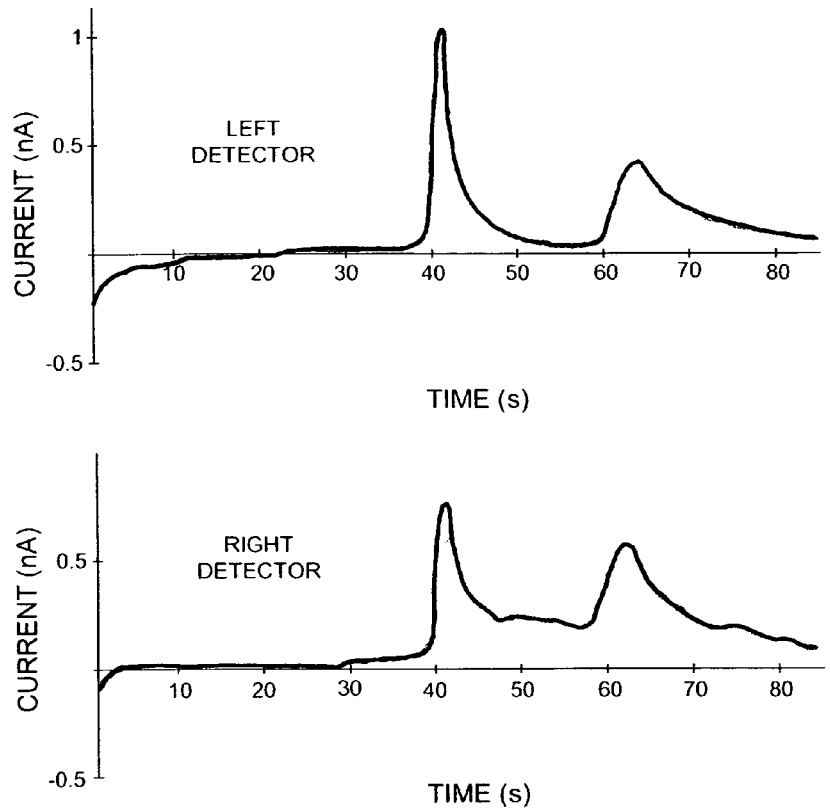
FIG. 11 illustrates data obtained from an example system of the invention.

FIG. 11 shows separation electropherograms for dopamine (4 mM) and catechol (4 mM) at both detectors of an example system of the invention. Phosphate buffer=20 mM; 6.5 pH. Capillary Electrophoresis Separation (driver) voltage=261 V; electrophoresis potential=+0.8 V vs. Pt reference electrode. The migration times obtained from example dual capillary electrophoresis system LOC devices for dopamine (39 sec) and catechol (59 sec) closely matched those obtained from single channel capillary electrophoresis systems of the prior art utilizing an identical detector as that of a capillary electrophoresis system of the invention having dual separation channels. Hydrodynamic voltammogram measurements revealed that the maximum detection peak was obtained at an optimum electrochemical detector reference voltage range of 0.8 V to 1.0 V vs. Pt electrode for dopamine.

Thus, an example capillary electrophoresis system of the invention provides a novel multiple separation channel system. The example system enables the simultaneous separation and detection of multiple analytes from a single sample. Example systems are useful for the detection of different species of analytes which require different electrode materials. Also, example systems provide instrumentation redundancy for analyte detection verification, as demonstrated above.

Methods of the Invention

Figure 12:
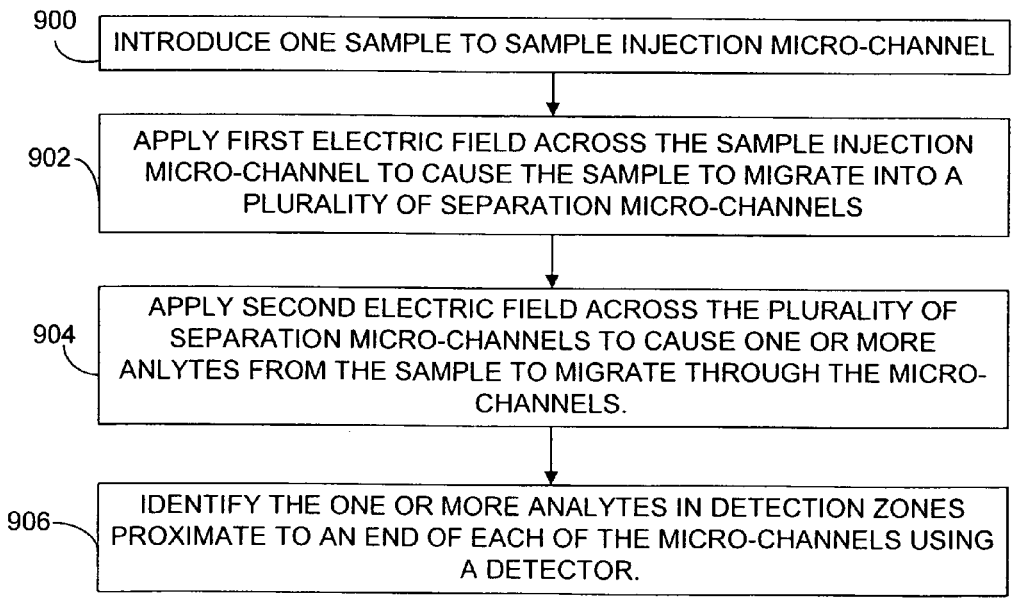
FIG. 12 is a flowchart illustrating example steps of one example method of the invention.

Other embodiments of the invention are directed to methods. Some methods of the invention, for example are directed to methods for using a capillary electrophoresis system of the invention. FIG. 12 is a flowchart illustrating some steps of one example method for performing capillary electrophoresis. One sample is introduced into a sample loading micro-channel. Block 900. A first electric field is applied across the sample loading micro-channel to cause the sample to migrate through the loading micro-channel and into a plurality of separation micro-channels. Block 902. A second electric field is applied across the plurality of separation micro-channels to cause one or more analytes from the sample to migrate through the separation micro-channels. Block 904. The one or more analytes are then identified in a detection zone proximate to an end of each of the micro-channel ends using a detector. Block 906.

A method of the invention including that illustrated in FIG. 12 may be used with any system of the invention, including any of the systems described and illustrated herein above. Further steps of methods of the invention, therefore, may include using use of additional elements of the systems as have been described herein. For example, additional steps of other example methods of the invention may include using a single power supply to perform loading and separation, applying substantially equal currents across all micro-channel legs, performing redundant testing by using multiple detectors that are substantially identical to one another, etc., as has been discussed herein above. It will be appreciated that discussion made herein above with regard to example systems of the invention, including the example system 10 of FIGS. 1-7, 110 of FIG. 8, or 300 of FIG. 9, may likewise be useful to describe methods of the invention.

Still another method of the invention is directed to detecting at least two different analytes from a single sample that have substantially identical electrophoretic mobilities. In addition to the steps described in FIG. 12, an additional step of this example method includes using different first and second detectors, with one configured to identify one of the two analytes and the second detector configured to identify the second. The detectors may be configured differently by, for example, functionalizing one or more of the electrodes of each through use of different materials of construction, application of a different catalyst layer, or the like.

While various embodiments of the present invention have been shown and described, it should be understood that these example embodiments are provided for illustration of the invention only, and should not limit the scope of the invention as claimed. Many modifications, substitutions and alternatives will be apparent to those knowledgeable in the art. By way of example and not limitation, although example capillary electrophoresis system embodiments have been described as being highly portable, miniaturized systems (including an LOC), other example embodiments may be larger bench scale systems. Capillary electrophoresis systems of the invention are likewise not limited to any particular number of separation channels, although examples have been described herein that include two and six. Various features of example embodiments of the invention are set forth in the following claims.

What is claimed is:

1. A capillary electrophoresis system comprising:
a plurality of separation channels configured to carry a buffer solution;
a single shared buffer reservoir communicating with all of the plurality of plurality of separation channels and containing the buffer solution;
a sample loading channel communicating with each of said plurality of separation channels;
a loading circuit comprising a plurality of electrodes configured to induce an electric field across said sample loading channel sufficient to deliver a sample to said plurality of separation channels;
a plurality of detectors, one each of said plurality of detectors proximate to each of said separation channels and configured to detect an analyte;
a driver circuit comprising a plurality of electrodes configured to induce an electric field across each of said plurality of separation channels, said electric field useful to cause analytes from said samples to migrate in each of said plurality of separation channels towards one of said detectors; and,
at least a controller configured to record data from each of said plurality of detectors, to control said plurality of detectors, and to control said driver circuit; wherein said sample loading channel is defined by a plurality of legs, each leg having substantially the same electrical resistance when they contain the same fluid.

2. A capillary electrophoresis system as defined by claim 1 wherein said loading channel and said plurality of separation channels communicate at intersections, said loading circuit configured to deliver a sample plug to each of said plurality of intersections, and wherein said plurality of separation channels and said loading channel are configured to result in substantially equal current flowing through each of said plurality intersections when said driver circuit is operated.

3. A capillary electrophoresis system as defined by claim 1 wherein each of said plurality of separation channels have substantially identical lengths and cross sectional dimensions, and are in communication with one another through a shared buffer reservoir.

4. A capillary electrophoresis system as defined by claim 1 wherein:
said separation channels each have an end and each communicate with said sample loading channel at an intersection;
wherein said plurality of electrodes includes one centrally positioned anode proximate to each of said intersections and a plurality of cathodes, one of said plurality of cathodes proximate to each of said channel separation channel ends; and,
wherein said one anode and said plurality of cathodes are configured to apply a substantially equal electrical field across each of said separation channels.

5. A capillary electrophoresis system as defined by claim 1 and further comprising:
a single sample reservoir communicating with said sample loading channel and containing a supply of said sample.

6. A capillary electrophoresis system as defined by claim 5 wherein a first electrical resistance between each of said detectors and said sample reservoir is substantially equal to a second electrical resistance between each of said detectors and said buffer reservoir, and wherein said first and second electrical resistances are substantially equal to a third electrical resistance between each of said detectors and said waste reservoir.

7. A capillary electrophoresis system as defined by claim 6 and further comprising a waste reservoir in communication with said sample loading channel, and wherein a third electrical resistance between each of said detectors and said waste reservoir is substantially equal to said first and second resistances.

8. A capillary electrophoresis system as defined by claim 1 and further comprising:
a sample reservoir in communication with said sample loading channel and containing a supply of said sample;
a waste reservoir in communication with said sample loading channel;
wherein said sample loading channel communicates with each of said separation channels at an intersection; and,
wherein said sample loading channel is defined by a first leg extending between said sample reservoir and each of said intersections, a second leg extending between said waste reservoir and each of said intersections.

9. A capillary electrophoresis system as defined by claim 8 and wherein:
each of said plurality of separation channels includes a third leg extending between said intersections and said buffer reservoir, each of said third legs having the same electrical resistance as said first and second legs when said first, second and third legs contain said buffer.

10. A capillary electrophoresis system as defined by claim 9 and wherein each of said plurality of separation channels includes a fourth leg extending between said detector and said intersections, each of said fourth legs having the same electrical resistance as said first, said second, and said third legs when said first, second, third and fourth legs contain said buffer.

11. A capillary electrophoresis system as defined by claim 10 wherein said first, second, third and fourth legs each have substantially the same length and cross sectional dimensions.

12. A capillary electrophoresis system as defined by claim 1 wherein each of said driver circuit and said loading circuit further comprise a common power supply connected to each of said driver circuit plurality of electrodes and to said loading circuit plurality of electrodes, said power supply comprising one or more switch mechanisms having a first state that connects said common power supply to said driver circuit and having a second state that connects said common power supply to said loading circuit.

13. A capillary electrophoresis system as defined by claim 1 wherein each of said plurality of separation channels has a single detector associated with it, wherein at least one of said plurality of detectors is configured to identify a first analyte and wherein at least a second of said plurality of detectors is configured to identify a second analyte, said first and second analytes having a substantially equal mobility, wherein the capillary electrophoresis system may be used to identify different analytes from one sample that have substantially equal mobilities when said at least one of said detectors associated with a first of said plurality of channels is used at the same time that said at least a second detector associated with a second of said plurality of channels is used.

14. A capillary electrophoresis system as defined by claim 1 wherein said plurality of separation channels, said sample loading channel, said driver circuit, and said plurality of detectors are of a miniature scale and are arranged on a micro-chip to form a lab on a chip.

15. A system for detecting one or more analytes as defined by claim 1 and further comprising:
a detector reservoir communicating with an exit of each of said plurality of separation channels and having a width that is greater than a width of said plurality of separation channels; and,
wherein each of said plurality of detectors are substantially identical electrochemical detectors placed proximate to a separation channel exit and are configured to detect one or more of said analytes through a reduction/oxidation reaction after said analytes pass from said separation channel exit.

16. A system for detecting one or more analytes as defined by claim 1 and further comprising:
a plurality of detector reservoirs, one each of said detector reservoirs communicating with an exit of each of said plurality of separation channels; and,
a plurality of shelf areas, one each of said shelf areas communicating with each of said plurality of separation channel exits and with each of said detector reservoirs, said plurality of shelf areas having a width greater than the width of said plurality of separation channels.

17. A portable lab on a chip capillary electrophoresis system for simultaneously separating and detecting multiple chemical/biochemical analytes arranged on a micro-chip, the system comprising:
at least two separation micro-channels communicating with a single buffer reservoir containing a buffer solution, each of said plurality of separation micro-channels having a channel exit;
a single sample loading micro-channel communicating at an intersection with each of said at least two separation micro-channels;
a sample reservoir in communication with said single sample loading micro-channel;
a waste reservoir in communication with said sample loading micro-channel;
a plurality of electro-chemical detector systems, one each of said systems proximate to each of said channel exits and including a detector reservoir communicating with each of said channel exits, each of said plurality of electro-chemical detector systems configured to detect analytes from a sample after they migrate through said channel exit;
a loading circuit comprising a first loading electrode in said sample reservoir and a second loading electrode in said waste reservoir, said loading circuit configured to cause current to flow through said sample loading micro-channel sufficient to cause said sample to migrate through said sample loading micro-channel;
a driver circuit comprising a first driver electrode in said buffer reservoir, a plurality of second driver electrodes with one each arranged in each of said plurality of detector reservoirs, said driver circuit configured to cause a substantially equal current to flow through each of said at least two separation micro-channels and to cause analytes from said sample loading micro-channel to migrate through each of said intersections towards each of said channel exits;
a controller configured to control at least said driver circuit and said loading circuit; and,
wherein the electrical resistance between each of said channel exits and said sample reservoir, between each of said channel exits and said buffer reservoir, and said channel exits and said waste reservoir are substantially equal.

18. A portable lab on a chip capillary electrophoresis system as defined by claim 17 and further comprising:
one common power supply; and,
a switch mechanism configured to switch said common power supply between powering said driver circuit and said loading circuit.

19. A portable lab on a chip capillary electrophoresis system as defined by claim 17 wherein the system is contained in a handheld housing, said housing further including a display for displaying data, data entry means for entering data and operating said controller, a memory, and a plurality of ports, one each of said plurality of ports communicating with one each of said sample reservoir, said waste reservoir, and said buffer reservoir.

20. A method for performing capillary electrophoresis comprising the steps of:
introducing one sample into a single sample loading micro-channel;
applying a first electric field across said single sample loading micro-channel to cause said one sample to migrate through said single loading micro-channel and into a plurality of separation micro-channels that each communicate with said single sample loading micro-channel;
applying a second electric field across said plurality of separation micro-channels to cause a buffer contained in a single buffer reservoir to flow into each of the plurality of separation micro-channels and to cause one or more analytes from said one sample to migrate through said separation micro-channels; and,
identifying said analytes from said one sample in a plurality of detection zones, one each proximate to an end of each of said separation micro-channels using a detector; and, wherein said sample loading channel is defined by a plurality of legs, each leg having substantially the same electrical resistance when they contain either the same fluid.

21. A method for performing capillary electrophoresis as defined by claim 20 wherein the method is for obtaining redundant test results from a single sample, and wherein the step of identifying said analytes using said detector comprises using an identical detector proximate to each of said separation micro-channel exits whereby results from a first of said plurality of separation micro-channels are redundant with results from a second of said plurality of separation channels, and wherein the step of applying a second electric field across said plurality of separation channels comprises applying said second field to cause said samples to migrate in each of said plurality of separation channels at the same rate of migration.

22. A method for performing capillary electrophoresis as defined by claim 20 wherein the method is for identifying at least a first and a second analyte from said one sample that have substantially identical electrophoretic mobilities, and wherein the step of identifying said analyte using said detector comprises using a first detector proximate to said exit of a first of said separation micro-channel exits that is configured to identify the first analyte and using a second detector proximate to said exit of a second of said plurality of separation micro-channels that is configured to identify the second analyte at the same time that the first detector is used to identify said first analyte whereby the first and second analytes having the same mobility may be detected at the same time, one each of detected at the exit of one each of the plurality of channels.

* * * * *

UNITED STATES PATENT AND TRADEMARK OFFICE
CERTIFICATE OF CORRECTION

PATENT NO. : 7,988,839 B2  
APPLICATION NO. : 11/524357  
DATED : August 2, 2011  
INVENTOR(S) : Rathissh Dorairaj Page 1 of 1

It is certified that error appears in the above-identified patent and that said Letters Patent is hereby corrected as shown below:

In the Drawings:
FIG. 11, box 904, line 3          Please delete "anlytes" and insert --analytes-- therefor.

In the Specification:
Col. 4, line 25                   Please delete "LiOH.H$_2$0" and insert --LiOH·H$_2$0-- therefor.
Col. 6, line 33                   After "effects" please delete "and".

In the Claims:
Col. 24, line 46, Claim 20        After "contain" please delete "either".

Signed and Sealed this  
Third Day of January, 2012

David J. Kappos  
*Director of the United States Patent and Trademark Office*